United States Patent [19]

Keller

[11] 4,397,307
[45] Aug. 9, 1983

[54] CRANIAL EXTENSION HOLDER

[75] Inventor: Arnold Keller, Kaihude, Fed. Rep. of Germany

[73] Assignee: Waldemar Link GmbH & Co., Hamburg, Fed. Rep. of Germany

[21] Appl. No.: 181,380

[22] Filed: Aug. 22, 1980

[30] Foreign Application Priority Data

Sep. 13, 1979 [DE] Fed. Rep. of Germany ....... 2936966

[51] Int. Cl.³ .............................................. A61H 1/02
[52] U.S. Cl. ................................................ 128/76 R
[58] Field of Search ................................... 128/38–40, 128/44, 60, 64, 75, 76, 84, 92, 133, 134, 303 B, 97; 250/456; 378/180; 5/451

[56] References Cited

U.S. PATENT DOCUMENTS 3,596,656  8/1971  Kaute ............................ 128/92 BA
3,741,205  6/1973  Markolf .......................... 128/92 B
3,923,046  12/1975  Heifetz ........................... 128/84 R

FOREIGN PATENT DOCUMENTS 671580  2/1939  Fed. Rep. of Germany .... 128/84 B
140162  12/1960  U.S.S.R. ................................ 128/75
271713  5/1970  U.S.S.R. ............................. 128/92 B
633526  11/1978  U.S.S.R. ................................ 128/75

OTHER PUBLICATIONS

Grutchfeld Traction Tongs, BS–902; Jul. 1952, Journal of Bone & Joint Surgery.
Skull Traction Apparatus; p. 522; Journal of Bone & Joint Surgery; 4/1948.

Primary Examiner—Richard J. Apley
Assistant Examiner—David J. Brown
Attorney, Agent, or Firm—Prutzman, Kalb, Chilton & Alix

[57] ABSTRACT

The pins of a cranial extension holder engage indirectly in bitemporal cranial bores by means of plastic sleeves which cover the wound with a flange and, due to the conicity or splayability of the pin, make clean contact with the surface of the bore. Relative movements between the sleeves and the bores are prevented since the pin is rotatable relative to the bracket. The pins are adjustable in their longitudinal direction in the bracket which is constructed without joints.

11 Claims, 4 Drawing Figures

U.S. Patent    Aug. 9, 1983    4,397,307
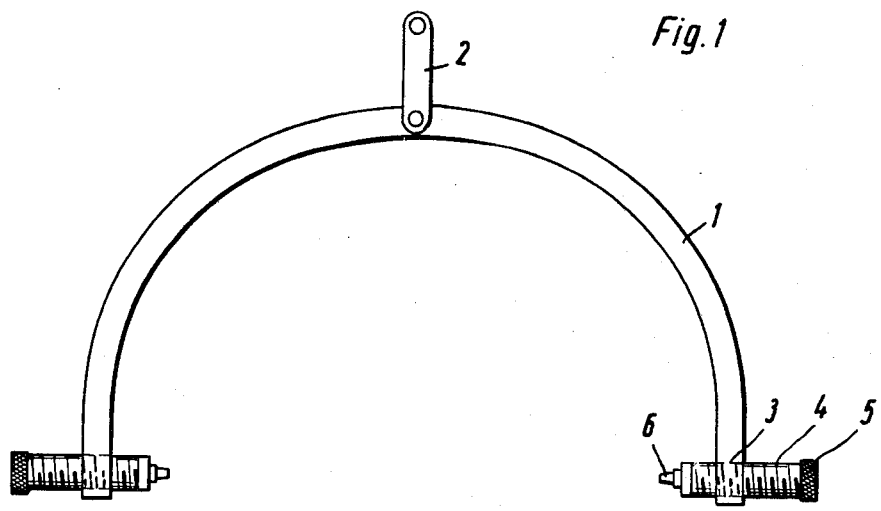
Fig. 1
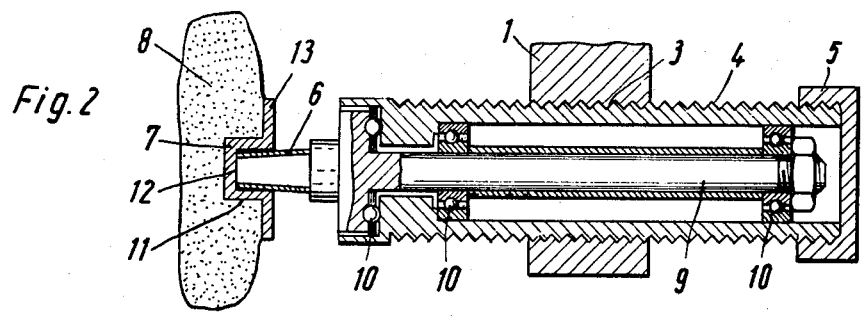
Fig. 2
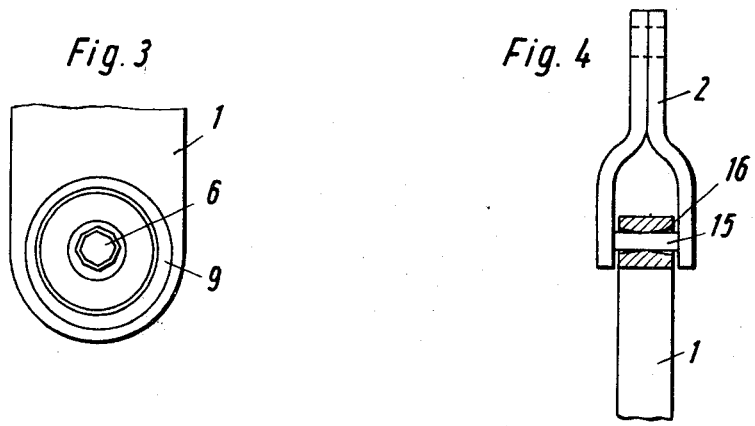
Fig. 3
Fig. 4

CRANIAL EXTENSION HOLDER

DESCRIPTION

The invention relates to a cranial extension holder having two pins, for insertion into bitemporal cranial bores, on the ends of a bracket which can be connected to the extension rope by means of an eye.

Known cranial extension holders (Crutchfield clamp and modifications; Archiv für orthopädische und Unfall-Chirurgie, Volume 47, pages 227–241, 1955) comprise a bracket consisting of two lever arms which are pivotally connected to one another in the middle and can be connected at the hinge to the extension rope and which carry, at the end, two pins pointing essentially towards each other and are connected by a spindle for adjusting the distance of the pins. For application, holes are drilled on both sides into the cranial bone by means of drilling instruments, the pins being inserted into the holes of the cranial extension holder to which subsequently the extension rope with the extension weight is fixed. The drilling wounds for the engagement of the pins of the cranial extension holder must remain open for the period of extension which in some cases lasts several months. There is a risk of infection since it is difficult to cover these wounds. It is also possible that necrotic symptoms appear on the cranial bone in the region of the bore, due to contact with the metal pin. Moreover, a risk of perforation of the cranial bone with a lesion of the dura is not excluded.

It is the object of the invention to provide a cranial extension holder of the type initially set out, which permits better covering of the wound and more favourable transmission of the force to the bone.

According to the invention, this object is achieved when, for each pin, a sleeve is provided which is to be inserted into the cranial bore and which has a hole, closed at the inner end, for receiving the pin and which preferably has, on the outer end, a flange for covering the wound. Advantageously, this sleeve consists of a yielding polymeric or elastomeric material.

The sleeve is more readily adaptable to the conditions of the wound. Particularly when it is provided with an outer flange, it permits a better closure of the wound than the pin. The transmission of force to the cranial bone then takes place over a surface area which relatively is larger and is uniformly adapted to the cranial bore. The sleeve is exactly adapted to the bore even if the two bores are not precisely aligned with one another, since it is possible to compensate alignment faults in the engagement between the sleeve and the pin. The adaptation is facilitated by the fact that the sleeve material is yielding to a certain extent, that is to say it is somewhat softer than the cranial bone, so that, in the case of differences in shape, these can be compensated up to a certain degree by deformation of the sleeve. Local peak forces are thus avoided, in favour of a more uniform transmission of force over a larger surface area. It is also an important point here that any possible relative movements between the cranium and the bracket do not necessarily change the position of the sleeve relative to the bore in the cranial bone since the relative movements can be absorbed at another point, for example between the sleeve and the pin or between the pin and the bracket.

Advantageously, the pin is conical or splayable. In this way, the sleeve is forced outwards and brought into full-face contact with the wall of the bore. This results in a clean closure of the wound and in a favourable transmission of force. Moreover, a splayable design of the pin can have the result that the sleeve is anchored in its longitudinal direction in the bore and, if appropriate, the pin in turn is also anchored in its longitudinal direction in the sleeve so that the pin can be reliably prevented from jumping out of the cranial bore under relatively small lateral pressure forces.

Advantageously, the pin is arranged to be rotatable about its longitudinal axis in the bracket so that any possible relative movements at this point between the cranium and the cranial holder can be absorbed without impairing the secure and unchanged position of the pin and the sleeve in the cranial bore. Since it is thus not necessary to make a relative rotation between the pin and the sleeve possible, it is in general advantageous also reliably to prevent such a rotation, so that the pin cannot penetrate further in an undesirable manner. For this purpose, the cross-sectional shape of the pin can deviate from a circular cross-section. For example, its cross-section can be of polygonal shape. In this way, a relative rotation between the sleeve and the pin is prevented.

According to the invention, it can also be advantageous when the pin is adjustable in its longitudinal direction in the bracket (not shown). This allows an adaptation to different cranial dimensions and an adjustment of the lateral pressure force in order to secure the pins in the cranial bores. This also makes it possible to construct the bracket without joints, according to the invention, so that the bracket is lighter and has a simpler shape and is easy to handle. The connection of the bracket to the eye for fixing the extension rope is advantageously provided by a universal joint, that is to say the connection is pivotable in any direction to a certain degree, so that injurious influences of movements on the cranial bone are avoided.

In the following text, the invention is explained in more detail by reference to the drawing which illustrates an advantageous example of an embodiment and in which:

FIG. 1 shows an overall view of the cranial extension holder,

FIG. 2 shows a partial section on a larger scale,

FIG. 3 shows an end view of the detail according to FIG. 2 and

FIG. 4 shows a section through the fixture of the eye of the bracket.

The bracket 1 is manufactured integrally and without joints from profiled tube, and it has therefore a light weight and is easy to handle. In the middle, it is pivotally joined to the connecting eye 2 and has, on its ends, threaded holes 3 in each of which a hollow spindle 4 is adjustable by screwing by means of a knurled extension 5 which also forms the cover of the hollow spindle. At its inward-pointing end, the hollow spindle carries the pin 6 which is of slightly conical shape and is delimited by an octagonal cross-section (see FIG. 3). In the applied state, the pin engages in the sleeve 7 which in turn is inserted into the bore in the cranial bone 8.

The pin 6 is seated on a shaft 9 which, by means of radial and axial bearings 10, is mounted in the hollow spindle 4 to be concentrically rotatable and axially undisplaceable.

The sleeve 7 consists of an essentially cylindrical part 11, of which the outer surface interacts with the surface of the cranial bore and the inner surface interacts with the outer surface of the pin 6. The inner end of the cylindrical part 11 is closed by the end wall 12. At the outer end, it carries a flange 13. The axial length of the cylindrical part has a dimension corresponding to the depth of the bore so that the flange 13 effects a clean closure of the wound on the outside. The sleeve is also capable of distributing undesirably high lateral pressure forces (forces in the axial direction of the pin) across the flange over a greater surface area of the cranium, so that the risk of perforation of the cranial bone with a lesion of the dura is excluded. Due to the enlarged surface area, the pressure distribution inside the bore is more favourable than in the case of direct action of the pin 6 on the wall of the bore.

The internal diameter of the sleeve in relation to the external diameter of the conical pin 6 is selected such that, when the pin is pressed into the sleeve, the latter is expanded radially and thus makes clean contact with the wound and enables the force to be transmitted over a large surface area. Undesirable relative movements between the sleeve and the surface of the wound are thus also prevented. The polygonal cross-section of the pin prevents relative rotation between the pin and the sleeve.

The connecting eye 2 is not only pivotable relative to the bracket 1, in a plane transversely to the fixing pin 15, but also to a certain degree in all other directions, since the bore 16 of the bracket 1, receiving the pin 15 is of double-conical design according to FIG. 4.

The plastic sleeves are preferably delivered in sterile packages to hospitals. The sleeves consist, for example, of high-molecular low-pressure polyethylene.

I claim:

1. In a cranial extension holder for insertion within opposed bitemporal cranial bores and having a generally U-shaped bracket with outer ends to be positioned on opposite sides of the cranimum, connector means mounted on the bracket for connecting the bracket for traction, a single pair of opposed insertion pins having inner ends for insertion within opposed bitemporal cranial bores, and pin mounting means mounting the insertion pins on the outer ends of the bracket in opposed alignment for insertion of the inner ends thereof into opposed bitemporal cranial bores, the improvement wherein the pin mounting means comprises bearing means for mounting the pair of opposed insertion pins on the bracket in opposed coaxial alignment on a fixed common axis for being freely rotatable about said common axis relative to the bracket without axial displacement of the pins relative to the bracket to permit angular displacement of the bracket about said common axis without angular or axial displacement of the insertion pins within the bitemporal cranial bores.

2. A cranial extension holder according to claim 1 wherein the inner end of each insertion pin is conical.

3. A cranial extension holder according to claim 1 wherein the inner end of each insertion pin is generally conical to secure the inner end within a bitemporal cranial bore.

4. A cranial extension holder according to claim 1 wherein the inner end of each insertion pin has a cross-sectional shape which is non-circular to secure said inner end against rotation within a bitemporal cranial bore.

5. A cranial extension holder according to claim 1 wherein the bracket is a jointless, rigid structure and wherein the bracket connector means comprises a connector link having a universal joint connection with the bracket.

6. A cranial extension holder according to claim 1, further comprising a mounting sleeve for each insertion pin, having a projection portion, for insertion into a cranial bore, with an outer bore, closed at its inner end, for receiving the inner end of the insertion pin.

7. A cranial extension holder according to claim 6, wherein the mounting sleeve has an outer peripheral flange surrounding said projection portion for covering the wound of the bitemporal cranial bore.

8. A cranial extension holder according to claim 6 or 7 wherein the sleeve is constructed of an elastomeric material.

9. In a cranial extension holder for insertion within opposed bitemporal cranial bores and having a generally U-shaped bracket with outer ends to be positioned on opposite sides of the cranium, connector means mounted on the bracket for connecting the bracket for traction, a pair of insertion pins mounted on the outer ends of the bracket and having inner ends for insertion within bitemporal cranial bores, and a mounting sleeve for each insertion pin, having a projection portion for insertion into a cranial bore, with an outer bore, closed at its inner end, for receiving the inner end of the insertion pin, and an outer peripheral flange surrounding said projection portion for covering the wound of the bitemporal cranial bore, the improvement wherein the inner end of each insertion pin has a cross-sectional shape which is non-circular to secure the inner end against rotation within the mounting sleeve.

10. In a cranial extension holder for insertion within opposed bitemporal cranial bores and having a generally U-shaped bracket with outer ends to be positioned on opposite sides of the cranimum, connector means mounted on the bracket for connecting the bracket for traction, a pair of insertion pins having inner ends for insertion within opposed bitemporal cranial bores, and pin mounting means mounting the insertion pins on the outer ends of the bracket in opposed alignment for insertion of the inner ends thereof into opposed bitemporal cranial bores, the improvement wherein the pin mounting means comprises bearing means for mounting the insertion pins for being freely rotatable about a common axis relative to the bracket without axial displacement relative to the bracket to permit angular displacement of the bracket about said common axis without angular or axial displacement of the insertion pins within the bitemporal cranial bores, and a mounting sleeve for each insertion pin, having a projection portion, for insertion into a cranial bore, with an outer bore, closed at its inner end, for receiving the inner end of the insertion pin, the inner end of each insertion pin being generally concial to splay the sleeve outwardly, upon insertion of the inner conical end of the pin therein, to secure the sleeve and inner end of the insertion pin within a bitemporal cranial bore.

11. In a cranial extension holder for insertion within opposed bitemporal cranial bores and having a generally U-shaped bracket with outer ends to be positioned on opposite sides of the cranimum, connector means mounted on the bracket for connecting the bracket for traction, a pair of insertion pins having inner ends for insertion within opposed bitemporal cranial bores, and pin mounting means mounting the insertion pins on the outer ends of the bracket in opposed alignment for insertion of the inner ends thereof into opposed bitemporal cranial bores, the improvement wherein the pin mounting means comprises bearing means for mounting the insertion pins for being freely rotatable about a common axis relative to the bracket without axial displacement relative to the bracket to permit angular displacement of the bracket about said common axis without angular or axial displacement of the insertion pins within the bitemporal cranial bores, and a mounting sleeve for each insertion pin, having a projection portion, for insertion into a cranial bore, with an outer bore, closed at its inner end, for receiving the inner end of the insertion pin, the mounting sleeve having an outer peripheral flange surrounding said projection portion for covering the wound of the bitemporal cranial bore, and the inner end of each insertion pin being generally conical to splay the sleeve outwardly, upon insertion of the inner conical end of the pin therein, to secure the sleeve and inner end of the insertion pin within a bitemporal cranial bore.

* * * * *